(12) United States Patent
Miller

(10) Patent No.: US 7,104,945 B2
(45) Date of Patent: *Sep. 12, 2006

(54) DEVICE FOR DEPOSITING ITEMS INTO TISSUE

(75) Inventor: Michael E. Miller, Trafalgar, IN (US)

(73) Assignee: Promex Technologies, LLC, Franklin, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/984,164

(22) Filed: Nov. 9, 2004

(65) Prior Publication Data

US 2005/0065393 A1    Mar. 24, 2005

Related U.S. Application Data

(63) Continuation of application No. 10/245,959, filed on Sep. 17, 2002, now Pat. No. 6,824,507, which is a continuation of application No. 09/531,922, filed on Mar. 21, 2000, now Pat. No. 6,450,938.

(51) Int. Cl.
*A61M 36/00* (2006.01)

(52) U.S. Cl. ......................................................... 600/7

(58) Field of Classification Search ................ 600/1–8; 606/142, 151, 185, 219
See application file for complete search history.

(56) References Cited

U.S. PATENT DOCUMENTS

| 4,105,030 | A | * | 8/1978 | Kercso | 604/506 |
| 4,700,692 | A | * | 10/1987 | Baumgartner | 600/7 |
| 6,450,938 | B1 | * | 9/2002 | Miller | 600/7 |
| 6,824,507 | B1 | * | 11/2004 | Miller | 600/7 |

* cited by examiner

Primary Examiner—John P. Lacyk

(57) ABSTRACT

The present invention provides devices for depositing objects into tissue of an animal. The devices include a cannula having a proximal end and an opposite distal end insertable into tissue and defining an exit aperture. The cannula has a sidewall between the distal and proximal ends and defines a passageway in communication with the exit aperture. A distal retaining tab extends from an inner surface of the cannula and is positioned across at least a portion of the passageway adjacent the exit aperture. The distal tab has a first closed position blocking the passageway and a second open position wherein the tab is urged towards the sidewall to allow an object to pass. The tab is resilient to return to the first position after the object passes the tab. In some embodiments, the invention also includes a proximal retaining tab adjacent the proximal end of the cannula and positionable to block a portion of the passageway. The invention also a stylet that is slidable within the passageway to urge the objects out through the exit aperture.

6 Claims, 7 Drawing Sheets

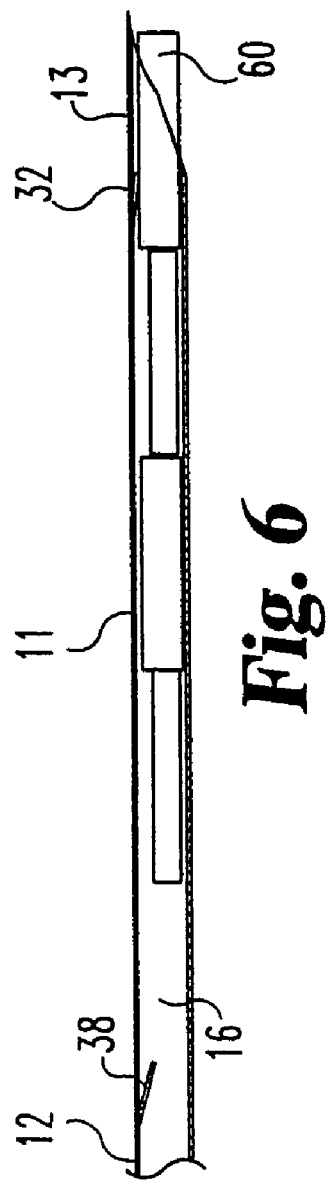
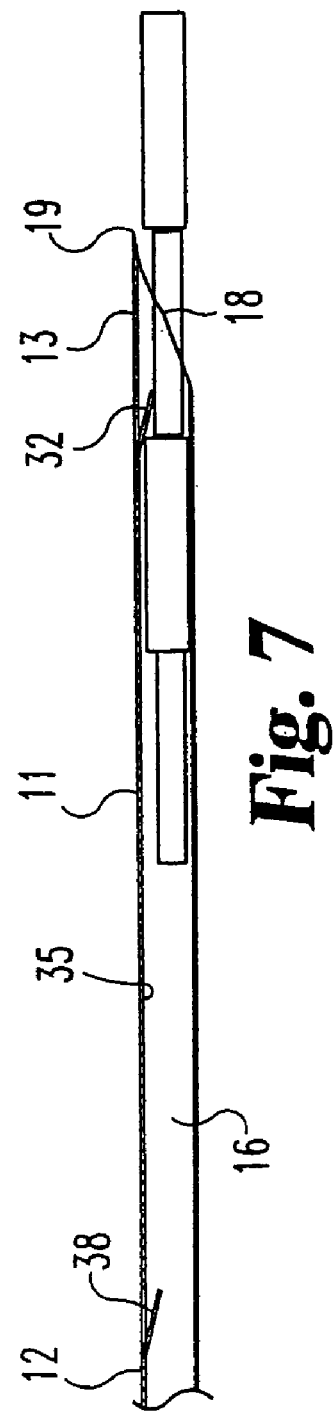

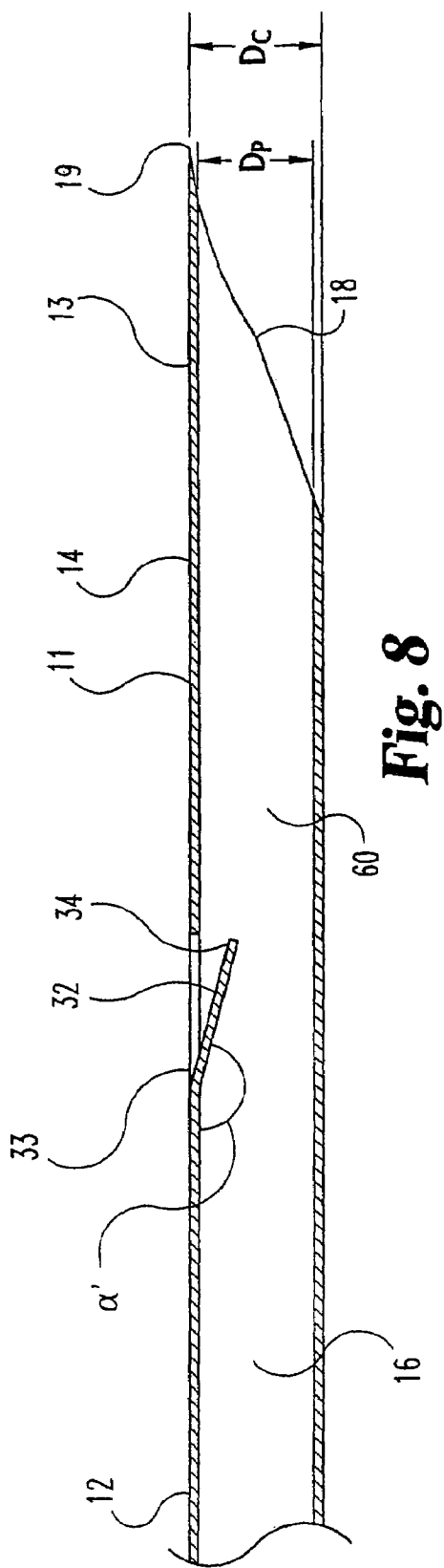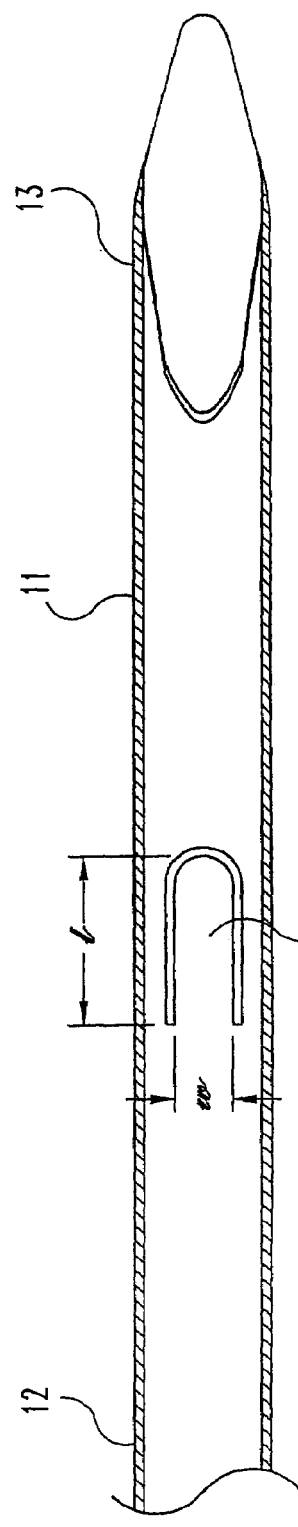
Fig. 8
Fig. 9

_US 7,104,945 B2_

DEVICE FOR DEPOSITING ITEMS INTO TISSUE

REFERENCE TO RELATED APPLICATIONS

This Application is a continuation of application Ser. No. 10/245,959, filed Sep. 17, 2002, now U.S. Pat. No. 6,824,507 which is a continuation of application Ser. No. 09/531,922, filed Mar. 21, 2000, now U.S. Pat. No. 6,450,938.

FIELD OF THE INVENTION

The present invention relates generally to the field of cancer treatment and specifically to brachytherapy.

BACKGROUND OF THE INVENTION

Prostate cancer is the most common malignancy in men and the second leading cause of cancer-related deaths. Traditional treatments have included radical prostatectomy and external-beam radiation therapy. Surgery has been the most common treatment because it is typically much more effective. Unfortunately prostatectomy is a major surgery that requires several days in the hospital and several months recuperation. As with all surgeries, there is a risk of complications, such as infection and uncontrolled bleeding. With prostatectomy, there is an additional risk of impotence or incontinence. Therefore, oncologists have sought alternatives.

Percutaneous prostate brachytherapy appears to be an ideal alternative to prostatectomy as a treatment for localized malignancies. It has already been effective in treating malignancies of other tissues, including cervix, breast, endometrium head and neck. In this procedure, radioactive pellets are deposited directly into the lesion through a long needle under visualization. Surrounding, healthy tissue is spared trauma from invasive surgery and radiation because the treatment is targeted. Moreover, brachytherapy is about as effective as prostatectomy without the long recuperation and risk of permanent side effects of surgery. Although brachytherapy is already recognized as an effective treatment for cancer, additional improvements are needed in areas such as isotope selection and dose and device design. For example, a problem would frequently occur when loading the needle with seeds and inserting the needle into the tissue. The seeds would prematurely exit the needle outside of the tissue or at inappropriate locations within the tissue.

In an effort to solve this problem, bone wax has been used to plug the end of the needle, and thus, prevent pellets from prematurely exiting the needle. Typically, about 0.05 cm is used, however, the amount can vary, which increases the uncertainty of the procedure. For example, in some cases the bone wax does not clear the needle tip, causing one or more seeds to be stuck within the cannula. In other cases, the pellet may stick to the wax at the tip of the needle, causing the pellet to be withdrawn with the needle.

The use of bone wax poses another significant disadvantage in that the wax is ultimately deposited into the tissue along with the pellets. Bone wax is not a tissue friendly substance because it is not absorbed by the body. Moreover, wax has been reported to aggravate existing infections and caused mild inflammatory reactions. As such, it is recommended by manufacturers that bone wax be used sparingly and that any excess bone wax should be removed from a surgical site. Furthermore, the long term ramifications of depositing bone wax into the body, especially the prostate, is not fully known. For example, introduction of a tissue irritant can result in fibrousing of the area, which may preclude the proper function of the urethra.

Another concern surrounding the use of bone wax, is that the wax causes the needle to be sticky and blunt. This decreases the needle's ability to pierce the prostate on contact. Consequently, as the needle is pressed forward against the prostate, the prostate moves forward several millimeters before the needle actually pierces the prostate. This movement of the prostate reduces the accuracy of intended pellet placement.

In an effort to solve the problem of controlling the exit of pellets from the needle, U.S. Pat. No. 5,810,769 to Schlegel and U.S. Pat. 5,281,197 to Arias disclose needles having a constricted portion, resulting in a narrowing of the hollow channel of the needle. The pellets are slightly larger in diameter than the narrowed portions of the needle, and therefore, the pellets are retained within the needle until they are forced through the narrowed portions. Although the constricted portions prevent the pellets from falling out and avoid the use of bone wax, the constrictions create a new set of disadvantages. As made clear by Schlegel, the pellets must have yielding or elastic properties to ensure that the pellets are not damaged. If the pellets are not elastic, the pellets may be damaged when forced through the constricted portion of the channel. A damaged pellet may result in the uncontrolled leaking of radioactive or medicinal substances from within the pellet. Another disadvantage of a needle having constricted portions is that the constrictions are not flexible, and therefore, the needle cannot accommodate a wide range of pellet sizes. If the pellets are too small, the pellets will slide right by the constricted portion, resulting in the pellets prematurely falling out of the distal end of the needle. On the other hand, if the pellets are too large, the physician may not be able to force the pellet beyond the constricted portions. Even if the large pellet is forced through the narrowed portion, the pellet may be seriously damaged in the process thereby lessening its effectiveness or safety within the tissue.

Another reference of interest is U.S. Pat. No. 4,105,030 to Kersco. The Kersco patent discloses a complicated gun-like, implant device for depositing multiple pellets. Kersco discloses a spring-activated retracting needle having a flexible finger at the distal tip. The flexible finger extends inward into the barrel of the needle, keeping the pellets retained in the needle until injection. After insertion of the needle into the target tissue, a spring mechanism retracts the needle from the tissue, leaving the pellets behind in the tissue. To be operable, the flexible finger located at the end of the barrel must be forced outward against the pressure of tissue and fluid as the needle is retracted. The device is incapable of depositing multiple pellets one at a time. More importantly, to the extent that the flexible finger can be forced outwardly into the tissue it may cause additional and unnecessary trauma.

Known systems designed to address the problem of pellets prematurely exiting the needle have done so only by creating a host of new problems. Therefore, a need has remained for a pellet implant device that can retain the pellets within the needle until ejection without the use of a wax, and that can individually inject multiple pellets of various sizes without causing unnecessary damage to the pellets or the tissue.

SUMMARY OF THE INVENTION

The present invention provides devices for depositing objects into tissue of an animal. The devices include a cannula having a proximal end and an opposite distal end insertable into tissue and defining an exit aperture. The cannula has a sidewall between the distal and proximal ends and defines a passageway in communication with the exit aperture. A distal retaining tab extends from an inner surface of the cannula and is positioned across at least a portion of the passageway adjacent the exit aperture. In one embodiment, the sidewall defines the distal tab. The distal tab has a first closed position blocking the passageway and a second open position wherein the tab is urged towards the sidewall to allow an object to pass. The tab is resilient to return to the first position after the object passes the tab.

In some embodiments, the invention also includes a proximal retaining tab adjacent the proximal end of the cannula and positionable to block a portion of the passageway.

The invention also provides assemblies that include the devices of the present invention and stylets for ejecting objects from the cannula. The stylet is slidable within the passageway to urge the objects out through the exit aperture.

One object of the present invention is to provide an improved pellet or seed implant device that can retain pellets within the needle until ejection without the use of bone wax. One advantage of the invention is that multiple pellets of various sizes can be injected individually without causing unnecessary damage to the pellets or the tissue. Another benefit of the invention is that it provides a tactile indication as each seed is ejected.

These and other objects, advantages and features of the present invention will become more apparent from the following description of the preferred embodiment.

DESCRIPTION OF THE FIGURES

FIG. 6 is a side sectional view of the device shown in FIG. 3 showing the tab in the open position.

FIG. 7 is a side sectional view of the device shown in FIG. 3 showing the tab returning to the closed position.

FIG. 8 is an enlarged side sectional view of the device shown in FIG. 1.

FIG. 9 is an enlarged partial top elevational view of the device shown in FIG. 1.

DESCRIPTION OF THE PREFERRED EMBODIMENTS

Figure 1:
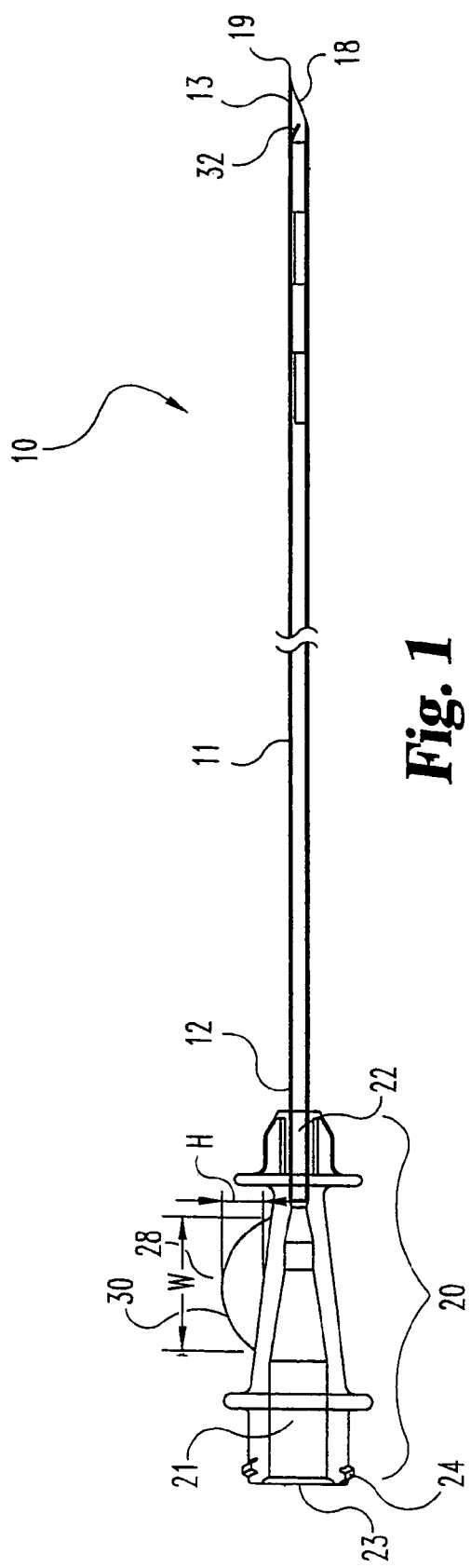
FIG. 1 is a side elevational view of a device according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides devices and methods for depositing objects such as radioactive pellets into tissue of an animal. The invention improves the safety, efficiency and efficacy of brachytherapy. Devices of the present invention have features that make the use of bone wax unnecessary thus avoiding tissue irritation and potential long-term implications of leaving a foreign material in the tissue of the patient. The devices provide a tactile indication for every seed that is deployed, which confirms the number of implanted seeds. In addition, the first seed is located at a precise location from the tip in each needle. This provides greater accuracy for seed placement. Also, because there is no interference from bone wax, the needle tip and each seed can be placed more accurately. Accurate placement of seeds is essential to optimize the dose to the target tissue while minimizing the dose to adjacent, healthy tissue. The ability to accurately place seeds also broadens the list of available isotopes, which vary in energy levels and thus, penetration of and efficacy to the target tissue as well as complications to surrounding tissue. In addition to all of the advantages described above, the present invention enhances the echogenicity of the needle so that the needle is consistently visible to the surgeon. Thus, the present invention provides an improvement in the field of oncogenic radiation therapy.

Figure 2:
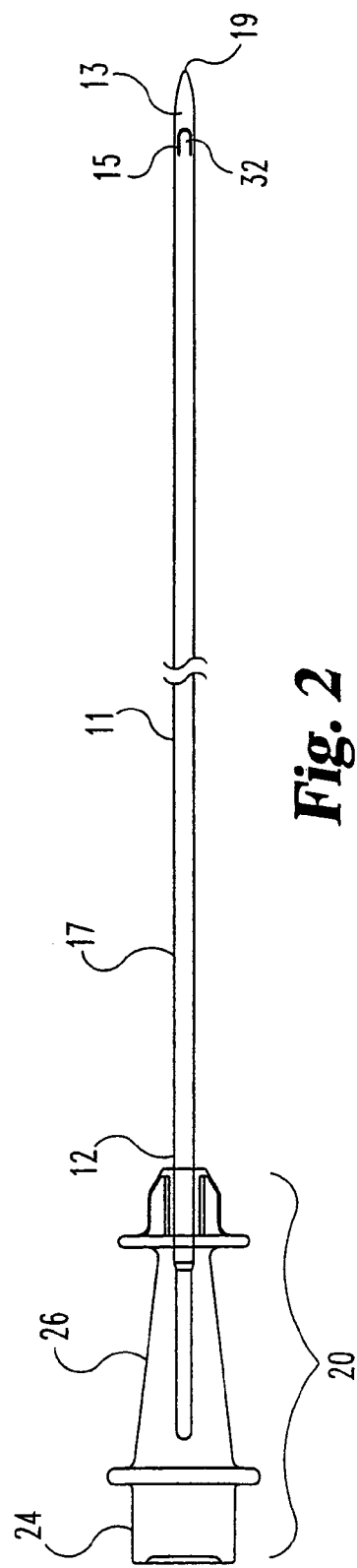
FIG. 2 is a top elevational view of the device shown in FIG. 1.

A preferred embodiment of the invention is shown in FIGS. 1 and 2. The device 10 includes a cannula 11 having a proximal end 12 and an opposite distal end 13, which is insertable into tissue. Adjacent to the proximal end 12 of cannula 11 is a proximal portion 17 and adjacent to the distal end 13 of cannula 11 is a distal portion 15. The distal end 13 preferably, has a beveled tip 19.

Figure 3:
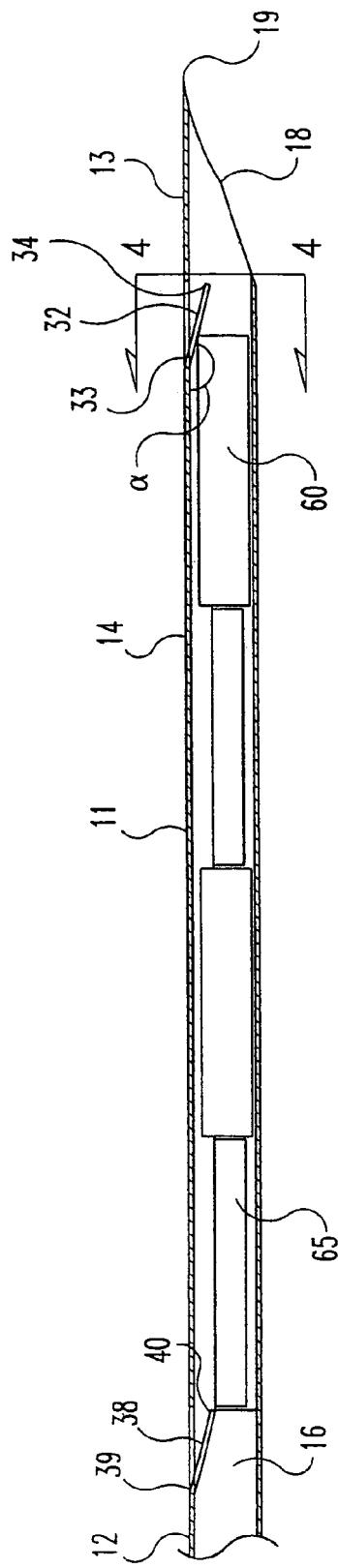
FIG. 3 is a partial side sectional view of the device shown in FIG. 1.
Figure 5:
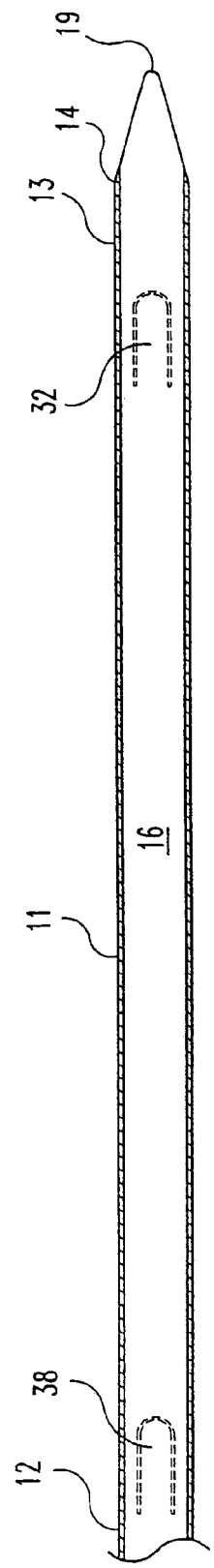
FIG. 5 is a partial top sectional view of the device shown in FIG. 1.
Figure 4:
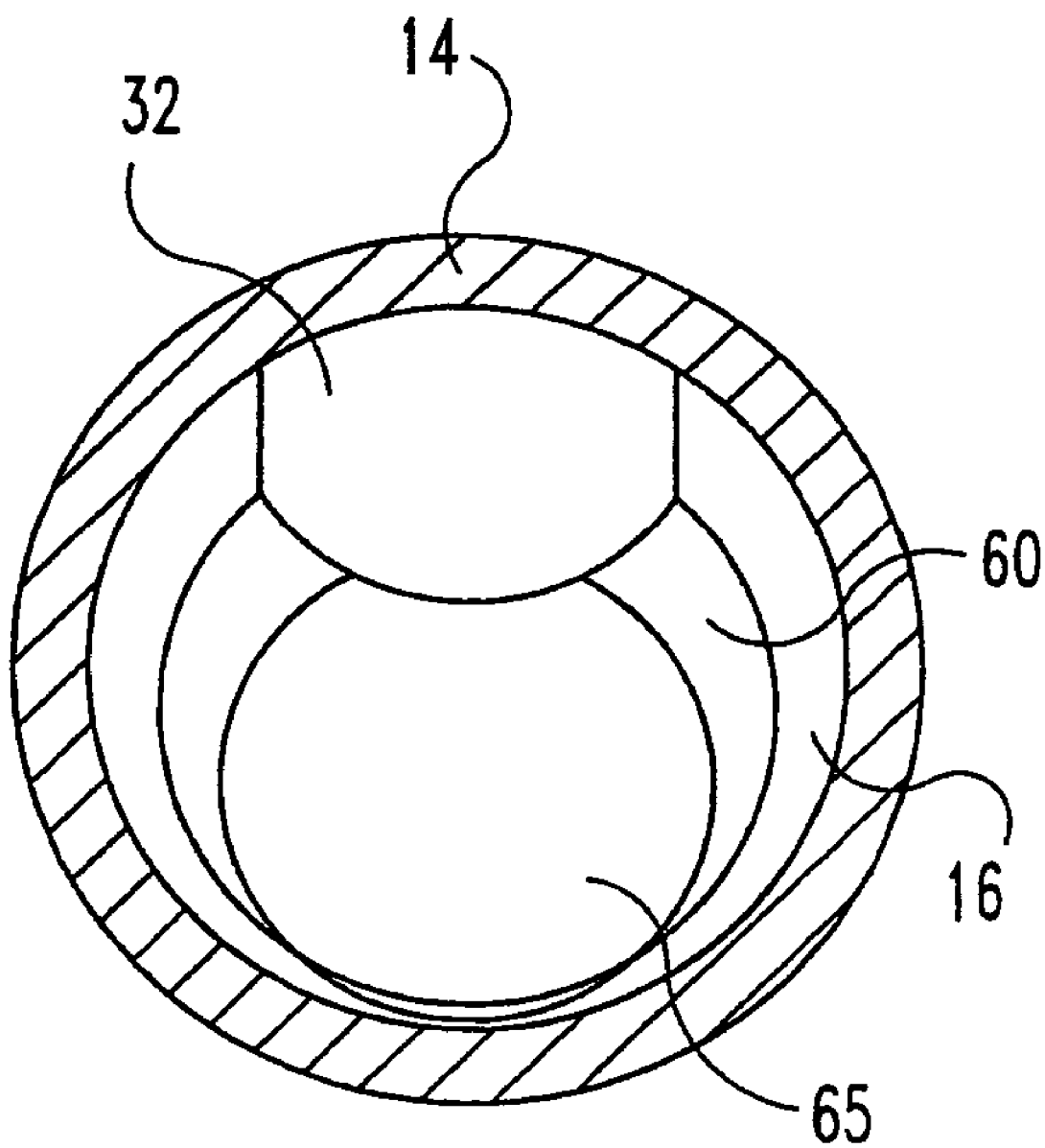
FIG. 4 is a partial cross-sectional view of the device shown in FIG. 3 taken along lines D—D.

Referring now to FIGS. 3–5, cannula has a sidewall 14 between the proximal end 12 and distal end 13. Sidewall 14 has an inner surface 35 and defines a passageway 16 in communication with an exit aperture 18 defined in the distal end 13 of the cannula 11. Passageway 16 extends between the distal 13 and proximal ends 14 and is sized and configured for receiving objects, such as, seeds 60 and spacers 65.

As shown in FIGS. 1 and 2, a hub 20 is attached to the proximal end 12 of the cannula 11. Hub 20 preferably defines a funnel-shaped channel 21 for delivering pellets and a stylet to the passageway 16. Channel 21 includes a first end 22 and a second end 23. The first end 22 of the channel 21 surrounds the proximal end 12 of the cannula 11 and is in communication with the passageway 16 of the cannula 11. The second 23 end of the channel 21 includes a fitting end 24 configured for engagement with a stylet.

Hub 20 preferably includes a gripping portion 26 as shown in FIG. 2. The gripping portion 26 is configured to be held by the practitioner during insertion and positioning of the cannula 11. The gripping portion 26, in preferred embodiments, has a tactile indicator means for positively indicating the orientation of the tip of the beveled exit aperture 18. The embodiment shown in FIG. 1, the hub 20 has a raised tactile indicator 28, which has a fixed relationship to the beveled tip 19 of the distal end 13 of the cannula 11. In this embodiment, the indicator 28 is a raised rounded rib 30. The rib 30 has a width W less than about one fifth the outer diameter of the gripping portion 26 of the hub 20 and a peak height H less than about one third the outer diameter of the gripping portion 26.

The present invention provides means for retaining objects within the passageway 16. In a preferred embodiment, a distal retaining tab 32 is provided inside of a distal portion 15 of the sidewall 14. The distal retaining tab 32 preferably flexible and is positionable across at least a portion of the passageway 16 as shown more clearly in FIGS. 3 and 4. In preferred embodiments, the distal tab 32 is formed from a cut out defined in the sidewall 14 as shown more clearly in FIG. 5. However, the invention contemplates any type of a distal retaining tab that extends from an inner surface of the distal portion 15 of the sidewall 14. For example, the tab could be affixed to the inner surface 35.

Referring again to FIG. 3, the distal retaining tab 32 has a first, proximal end 33 that is attached to, or is integral with, the cannula sidewall 14. An opposite distal end 34 of the tab 32 is free from and extends away from the sidewall 14 to releasably retain objects within the passageway 16 of the cannula 11. The distal retaining tab 32 has a first closed position blocking the passageway 16 as shown in FIG. 3 and a second open position wherein the tab 32 is urged towards the sidewall 14 to allow an object to pass A as shown in FIG. 6. In the open position, the distal end 34 of the tab will approach the sidewall 14. The tab is resilient to return to the first position after the object passes the tab 32 as shown in FIG. 7.

One advantage of this invention is that the devices of this invention can be conveniently and inexpensively configured to accommodate a cannula and objects of virtually any size and material. The tab 32 can be adjusted to support and retain an object or pellet of any size that will fit within the passageway 16 of the cannula 11. For smaller pellets it may be necessary to bend the tab 32 and form a smaller angle α to block a greater portion of the passageway 16. Heavier pellets may also require a smaller angle α in order to support the weight of the object within the cannula 11. For example, in the embodiment shown in FIG. 3, angle α is approximately 165° and the tab 32 blocks about one third of the passageway 16. The device shown in FIG. 8, however, has the tab 32 positioned to block slightly over half of the passageway 16 with an angle α' of about 155°.

The devices of this invention can be manufactured according to known manufacturing processes using known medical grade materials, such as stainless steel. The retention tabs of this invention can be formed by methods that are known in the art such as electro-discharge machining.

The dimensions of the cannula 11 and the retaining tab 32 will be selected based upon the particular application and the amount of force that is desirable to use to urge the pellets past the tab 32. For example, the thicker the sidewall 14 the stiffer the tab 32 will be. In one particular embodiment shown in FIGS. 8 and 9, the device is a brachytherapy device for the treatment of prostate cancer. The device includes an 18 gauge needle having a cannula 11 with a diameter $D_c$ of about 0.050 inches with a passageway 16 having a diameter $D_p$ of about 0.040 inches. The distal end 34 of the tab 32 is positioned about 0.039 inches from the distal end 12 of the cannula 11 and has a radius of 0.010. The tab 32 has a length l of about 0.065 inches and a width w of about 0.020 inches. As shown in FIG. 8, tab 32 is positioned to block approximately one half of passageway, however, tab 32 can be adjusted by the manufacturer or the surgeon as needed based upon the size and weight of the pellets.

Figure 10:
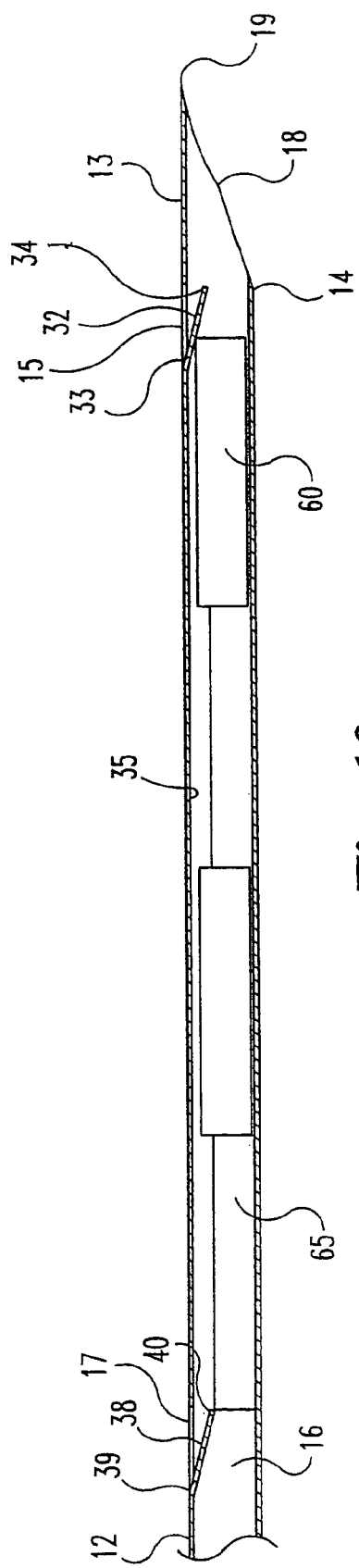
FIG. 10 is a partial cross-sectional view of another embodiment of this invention, which includes a proximal retaining tab.

In another preferred embodiment, the device also includes a proximal retaining tab 38 located on the inner surface 35 of the proximal portion 17 of the cannula 11. Referring to FIG. 10, similar to the distal retaining tab 32, the proximal retaining tab 38 has a first, proximal end 39 that is attached to, or is integral with, the cannula 11 sidewall 14. An opposite distal end 40 of the proximal tab is free from and extends away from the sidewall 14 to retain objects within the passageway 16 of the cannula 11. The proximal tab 38 is positionable across the passageway 16 to block at least a portion of the passageway 16. The proximal tab 38 traps seeds 60 or other objects within the passageway 16. The proximal tab 38 has a first closed position blocking the passageway 16 and a second open position wherein the tab 38 is urged towards the sidewall 14 in response to receiving an opening force from a stylet, which is pushed through the passageway 16 from an opening in the proximal end 12 of the cannula 11.

Figure 11:
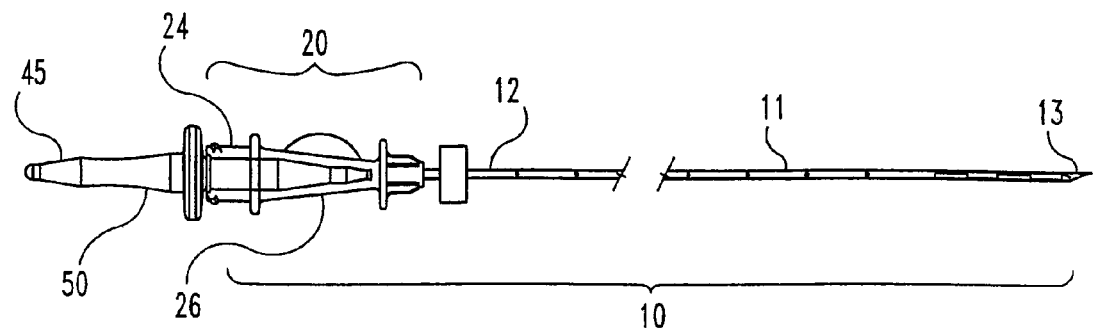
FIG. 11 is a side elevational view of an assembly according to this invention.
Figure 12:
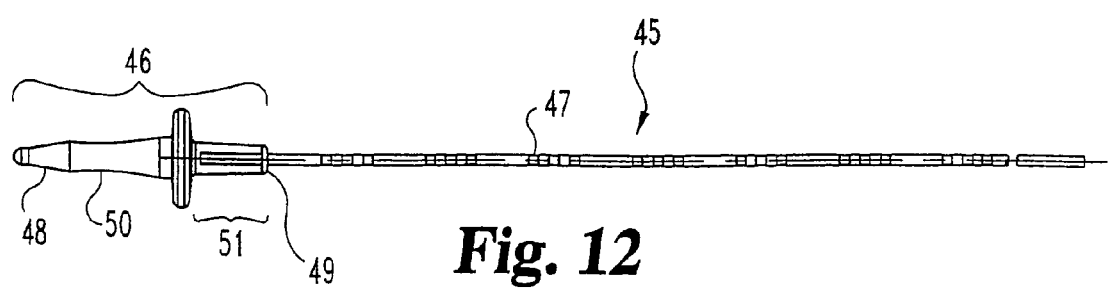
FIG. 12 is a side elevational view of a stylet according to this invention.

The invention also provides assemblies including the devices of this invention. An assembly according to one embodiment is shown in FIG. 11 and includes a device 10 of this invention and a stylet 45 slidable within the passageway 16 of the cannula 11 to urge objects out through the exit aperture 18. In embodiments that employ a proximal retaining tab 38, the stylet 45 will urge the proximal tab 38 towards the sidewall 14 to approach the seeds within the cannula 11. The stylet 45 as shown in FIG. 12, includes a handle 46 and a shaft 47. The shaft 47 is sized and configured to be received within the passageway 16 of the device 10. The handle 46 of the stylet includes a proximal end 48 and a distal end 49. The proximal end 48 of the handle 46, preferably, includes a gripping portion 50 configured to be held by the practitioner. The distal end 49 of the handle 46 is attached to the shaft 47. Adjacent the distal end 49 of the handle 46 is a distal portion 51, which is configured to be received within the fitting end 24 of the hub 20 of device 10 when the stylet 45 is slidably engaged within the cannula 11 of device 10.

In operation, the patient is prepared according to conventional operating procedures for brachytherapy or any other relevant procedure. For example, patients having prostate cancer are clinically staged and then counseled about treatments that available and appropriate. If the patient selects ultrasound-guided transperineal brachytherapy, studies are performed to determine the prostate volume and shape as described in Grimm, 1994 (*New Techniques in Prostate Surgery*, Volume 2, pages 113–125). The radiation oncologist then determines the number of seeds required and the isotope to be used. The patient is instructed to maintain a clear diet for 48 hours before the procedure with nothing by mouth after midnight with a Fleets phosphsoda the night before and a Fleets enema two hours before the procedure. The patient is also given a broad-spectrum antibiotic intravenously and a spinal anesthesia. The operating room is set up and the patient is prepared as described by Grimm 1994.

A device of the present invention is loaded with seeds, typically 2–6, and spacers as needed. Because the device includes a distal retention tab, it is not necessary to seal the distal end with bone wax. In some cases, it may be necessary to adjust the tab to support and retain the seeds. The proximal retaining tab is then bent into place to prevent the seeds from falling out of the proximal opening of the cannula. An ultrasound probe, stepping unit, stabilization apparatus and template coordinate grid are all positioned and adjusted as known in the art and described by Grimm 1994.

The cannula is inserted into the prostate at pre-planned locations or coordinates. Care is taken to ensure that the distal end of the needle is positioned precisely. Precise placement is enhanced using the present invention because the first seed is always in a known location within the passageway unlike prior art devices, which require the use of bone wax. When wax is forced into the exit aperture of the cannula, the amount of wax that is caught within the aperture is variable. The physician is never entirely certain how deep the wax plug extends into the passageway. Of course, the depth of the wax plug determines the location of the first seed. The present invention solves this problem because the location of the first seed is always known and can be easily determined by examining the outer surface of the cannula to determine the location of the retention tab.

Once the cannula is properly positioned, the tip of the stylet is placed through the hub of the device and into the passageway. The stylet is then pushed past the proximal retention tab until the tip reaches the first seed or spacer. Withdrawing the cannula over the stylet results in the first seed pushing past the distal retaining tab and then being ejected into the tissue. Typically, using prior art devices and methods, the length from the hub of the stylet to the hub of the needle is measured to determine when and how many seeds and spacers have been ejected. The present invention, however, provides a tactile indication each time a seed is deployed. As the seed passes the retention tab it causes a discrete tactile "pop" and the physician knows that the seed has been ejected. After all of the seeds have been implanted, the placement of the seeds is confirmed.

The present invention shall be more concretely explained with the following example, which is to be considered merely representative of the present invention and thus should not be considered as limiting.

EXAMPLE

Brachytherapy devices were manufactured according to the present invention. The devices were used in two ultrasound-guided transperineal implantation procedures (as described above). The procedures were performed on human patients by two oncologists, a physicist and an urologist. The devices of this invention were evaluated by the surgical staff to determine whether the invention eliminated the need for bone wax and whether the devices of this invention perform as well as a known competitive device that requires the use of bone wax.

The devices of this invention were used to perform both procedures and the following observations were made by the surgical staff.

1. In the first surgical case, six seeds and spacers were loaded into the cannula. It was noted that the distal tab could not initially support the entire column of seeds and spacers. The tab was then bent to reduce the angle between the tab and the sidewall and was found to support the column.

2. The devices were inserted without incident. Tissue did not core up into the exit aperture of the cannula. The seeds and spacers were properly retained within the cannula during insertion.

3. The surgical staff observed a significant reduction in the insertion resistance of the device over the competitive product which requires bone wax. The amount of "pull back" resistance was found to be comparable to the prior art product. The result is more accurate needle placement because the prostate does not move away from the advancing needle tip. Ultimately, seeds can be placed more precisely, which leads to more effective treatment.

4. The surgical staff noted and was pleased with the tactile indications of the ejection of each seed and spacer. The tactile indication was observed to be very discrete and apparent and a significant improvement over the prior art devices, which provide only a subtle and "mushy" tactile indication at best.

5. The surgical staff determined that further testing is required to evaluate whether the device of this invention tracked any better or worse than the prior art device.

6. The feature of precise and reproducible placement of the first seed within the cannula was noted with enthusiasm as an advantage over prior art devices that require bone wax.

7. The devices of the present invention were as visible on ultrasound as the prior art devices and may have been slightly more visible than the competitive device.

8. It appeared that when using the devices of this invention, the seeds did not appear spring laterally as they do when ejected from prior art devices. This improved the accuracy of seed placement.

9. The seeds and spacers loaded equal to the prior devices.

Conclusions

The surgeries resulted in successful placement of the seeds into the malignant tissue. Both patients recovered from the procedure and reported no greater pain or discomfort than is typical for ultrasound-guided transperineal implantation procedures. The observations during, and after surgeries of the surgical staff and patients show that the present invention provides a significant improvement in the field of brachytherapy.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed:

1. A device for depositing objects into tissue of an animal, comprising:
   a cannula defining a passageway for the objects, an exit aperture in communication with said passageway; and
   a retaining element extending into said passageway, said retaining element proximate said exit aperture.

2. The device of claim 1, wherein said proximal portion defines a second retaining element tab positionable across at least a portion of said passageway.

3. A device for depositing objects into tissues of an animal, comprising:
   a cannula having a proximal end and an opposite end insertable into tissue, said cannula defining a passageway for the objects, an exit aperture in communication with said passageway; and
   a retaining element extending into said passageway between said proximal end and said exit aperture.

4. The device of claim 3, wherein said proximal portion defines a second retaining element positionable across at least a portion of said passageway.

5. A device for depositing objects into tissue of an animal, comprising:
   a cannula having a proximal end and an opposite distal end insertable into tissue and defining an exit aperture, said cannula having a sidewall between said proximal end and distal end and defining a passageway in communication with said exit aperture for the objects; and
   a retaining element offset from said distal end and extending into said passageway.

6. The device of claim 5, wherein said proximal portion defines a second retaining element positionable across at least a portion of said passageway.

* * * * *